(12) United States Patent
Pasupuleti et al.

(10) Patent No.: US 11,207,481 B2
(45) Date of Patent: Dec. 28, 2021

(54) ELECTRO-MECHANICAL RESUSCITATING APPARATUS

(71) Applicant: Biodesign Innovation Labs Private Limited, Bengaluru (IN)

(72) Inventors: Gautham Pasupuleti, Bengaluru (IN); Adithya Pasupuleti, Bengaluru (IN); Roshan Mohan, Bengaluru (IN)

(73) Assignee: BIODESIGN INNOVATION LABS PRIVATE LIMITED, Bengaluru (IN)

( * ) Notice: Subject to any disclaimer, the term of this patent is extended or adjusted under 35 U.S.C. 154(b) by 385 days.

(21) Appl. No.: 16/349,357

(22) PCT Filed: Sep. 13, 2018

(86) PCT No.: PCT/IB2018/056991
§ 371 (c)(1),
(2) Date: May 13, 2019

(87) PCT Pub. No.: WO2020/016639
PCT Pub. Date: Jan. 23, 2020

(65) Prior Publication Data
US 2020/0261672 A1    Aug. 20, 2020

(30) Foreign Application Priority Data

Jul. 17, 2018  (IN) .............................. 201841026645

(51) Int. Cl.
*A61M 16/00* (2006.01)
*A61M 16/20* (2006.01)

(52) U.S. Cl.
CPC .... *A61M 16/0084* (2014.02); *A61M 16/0051* (2013.01); *A61M 16/022* (2017.08); *A61M 16/209* (2014.02); *A61M 2016/0033* (2013.01); *A61M 2202/0208* (2013.01); *A61M 2205/07* (2013.01); *A61M 2205/8206* (2013.01)

(58) Field of Classification Search
CPC .......... A61M 16/0084; A61M 16/0078; A61M 16/0075; A61M 16/0081; A61M 16/006; A61M 16/0072
See application file for complete search history.

(56) References Cited

U.S. PATENT DOCUMENTS 10,639,442 B2 *   5/2020   Piracha ............... A61M 16/208
2012/0145151 A1 *  6/2012   Bergman .......... A61M 16/0078
                                                    128/204.21

(Continued)

FOREIGN PATENT DOCUMENTS

CN          103751894 A  *  4/2014

OTHER PUBLICATIONS

Piracha, 62666402 Specification,May 2018.*
International Search Report for PCT/IB2018/056991 dated Jul. 3, 2019.

*Primary Examiner* — Margaret M Luarca
(74) *Attorney, Agent, or Firm* — Thomas | Horstemeyer, LLP

(57) ABSTRACT

The present invention is a mechanical ventilation device which delivers intermittent positive pressure ventilation by compressing AMBU. As the device uses existing AMBU for the ventilation, it is intended to automate the process of hand ventilation and will hence keep the costs and skill requirement low. Due to usage of the AMBU and simple mechanics, it is easy to manufacture and maintain the device.

20 Claims, 5 Drawing Sheets

(56) References Cited

U.S. PATENT DOCUMENTS

2017/0197047 A1     7/2017   Minato et al.
2018/0021533 A1*   1/2018   Gausche-Hill ........ A61M 16/20
                                                                      128/205.14

* cited by examiner

ELECTRO-MECHANICAL RESUSCITATING APPARATUS

CROSS-REFERENCE TO RELATED APPLICATIONS

This application is a § 371 national phase application of PCT/IB2018/056991 filed Sep. 13, 2018, entitled "AN ELECTRO-MECHANICAL RESUSCITATING APPARATUS," which claims the benefit of and priority to Indian Patent Application No. 201841026645 filed Jul. 17, 2018, the contents of which being incorporated by reference in their entirety herein.

FIELD OF THE INVENTION

The present invention relates generally to the life-support Medical device for mechanical ventilation and particularly, relates to an electromechanical resuscitating apparatus for controlling expansion and compression of self-inflating bag.

BACKGROUND

Manual resuscitators using self-inflating bags or AMBU® bags are well recognized in the prior art. The AMBU®-bags or self-inflating bags are hand-held devices and are in wide-spread use in medical and emergency treatment of patients and commonly used to provide positive pressure ventilation to patients who are not breathing or not breathing adequately. They are designed for manually squeezing, such as by a doctor, nurse, orderly, EMT or other medical service provider. Their usage includes, for example, respiration a patient in the field and/or during transport to a hospital.

AMBU®-bags or self-inflating bags are primarily used for keeping a patient respirated during movement from one location to another or during procedures such as "cardio-pulmonary resuscitation", often times referred to as "CPR". During such procedure, it is necessary to supply the patient with large quantities of air or oxygen. In addition to forcing a volume of air to the patient, such devices must also take into account the fact that the patient may inhale or exhale under his or her own ability.

Use of manual resuscitators to ventilate a patient is frequently called 'bagging the patient', and is regularly necessary for medical emergencies when the patient's breathing is insufficient (Respiratory Failure) or has ceased completely (Respiratory Arrest). Use of the manual resuscitator force-feeds air or oxygen into the lungs in order to inflate them under pressure, thus constituting a means to manually provide positive-pressure ventilation. It is used by medical professionals in case of emergencies and during inter-hospital and intra-hospital transit of ventilator-dependent patients. In developing and under-developed countries, it is used for long durations mainly due to unavailability of an ICU bed with a ventilator or absence of a portable transport-ventilator. One major issue with this practice is that untrained persons, usually the patients care-taker is asked to do the bagging due to lack of trained staff. This results in the patient being ventilated at suboptimal and often unsafe rates of pressure and frequency for very long durations at the hands of the caretaker. There have also been a high number of instances where the caretaker gives-up bagging the patient from mere exhaustion of the monotonous and repetitive task.

Accordingly, there exists a need for a mechanism that overcomes the problems in the prior art and delivers Intermittent Positive Pressure Ventilation (IPPV) by mechanically compressing the self-inflating bag, and essentially automating the process of bagging. There is a long felt need for a cost-effective, portable, mechanism that ensures that the patients requiring a ventilator support get access to a safer alternative for prolonged manual ventilation at the peripheries.

BRIEF SUMMARY

The present invention relates to a Mechanical Ventilation device which delivers Intermittent Positive Pressure Ventilation (IPPV) by mechanically compressing the self-inflating bag, and essentially automating the process of bagging. The frequency of ventilation can be set by a trained medical professional and oxygen supplementation can also be given. The mechanical motion of the self-inflating compression mechanism is synthesized to deliver end values of pressure and frequency in-par with that delivered when given by a trained and experienced medical professional. In effect, the device simulates the effects of hand compression from a trained professional during ventilation. In an embodiment, an electro-mechanical resuscitating apparatus for controlling expansion and compression of a self-inflating bag is provided. The apparatus includes a first supporting arm and a second supporting arm 104, wherein each of the first supporting arm 102 and second supporting arm 104 includes a coupling end and a placement end respectively, wherein a length of the each supporting arm between the coupling end and the placement end conforms to at least a portion of an outer surface area of the self-inflating bag; a first coupling arm 110 and a second coupling arm 112 connected to each other through a plurality of connecting elements while maintaining a predetermined distance across respective lengths, wherein the first supporting arm is rotatably fixed at a first end between the first coupling arm 110 and second coupling arm 112 and the second supporting arm 104 is rotatably fixed at a second end 116 between the first coupling arm 110 and second coupling arm 112; a first driving mechanism and a second driving mechanism coupled to a first shaft 118 and a second shaft 120 respectively, wherein a front end of the first shaft 118 is coupled to the coupling end of the first supporting arm and a front end of the second shaft 120 is coupled to the coupling end of the second supporting arm 104, and a controller communicatively coupled to the first driving mechanism and the second driving mechanism, wherein the controller is configured to control the speed and direction of movement of the first shaft 118 and the second shaft 120 via the first driving mechanism and the second driving mechanism, wherein an actuation of the first shaft 118 and second shaft 120 in a first direction enables movement of the placement ends of the respective first supporting arm and the second supporting arm 104 against surface of the self-inflating bag causing compression of the self-inflating bag, wherein an actuation of the first shaft 118 and second shaft 120 in a second direction enables movement of the placement ends of the first supporting arm and the second supporting arm 104 to retract causing retraction of the self-inflating bag.

It is an object of the present invention to provide mechanism that uses an existing self-inflating bag for the compression, and provides a simpler mechanism to automate the process of hand ventilation and will hence keep the costs and skill requirement low.

It is an object of the present invention to provide mechanism that is easy to manufacture and maintain and cause minimal damage and wear and tear of the self-inflating bag.

It is an object of the present invention to provide mechanism to supply air to the patient by automatically compressing the self-inflating bag at conditions set by the user. By having a compressing mechanism with DC motor as a prime driver, a purely automated ventilation system is achieved. Various sensors are used to detect the working conditions of the system and a feedback loop is introduced to update the working as per requirements.

To further clarify advantages and features of the present invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings.

BRIEF DESCRIPTION OF FIGURES

These and other features, aspects, and advantages of the present invention will become better understood when the following detailed description is read with reference to the accompanying drawings in which like characters represent like parts throughout the drawings, wherein.

Figure 1A:
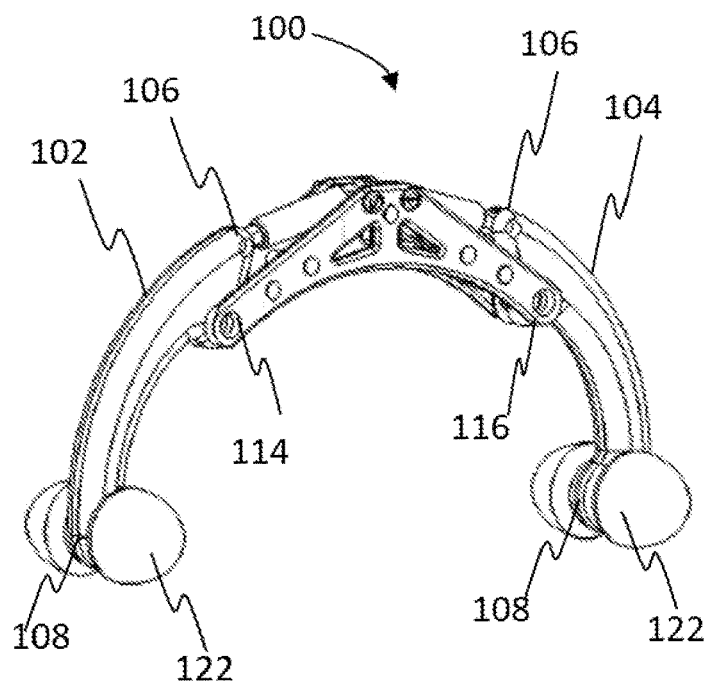
FIGS. 1(a)-1(d) show schematics of an electro-mechanical resuscitating apparatus for controlling expansion and compression of a self-inflating bag in accordance with an embodiment of the invention.
Figure 1B:
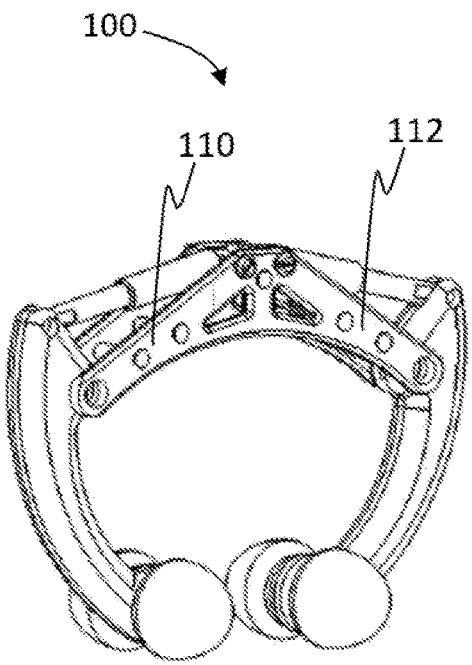
Figure 1C:
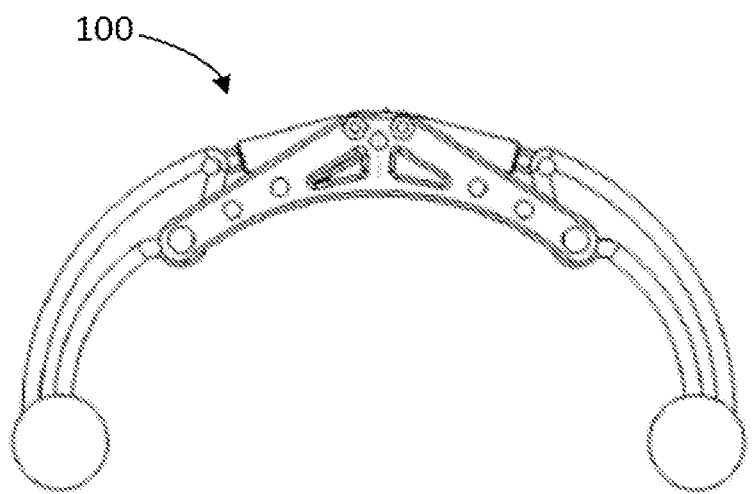
Figure 1D:
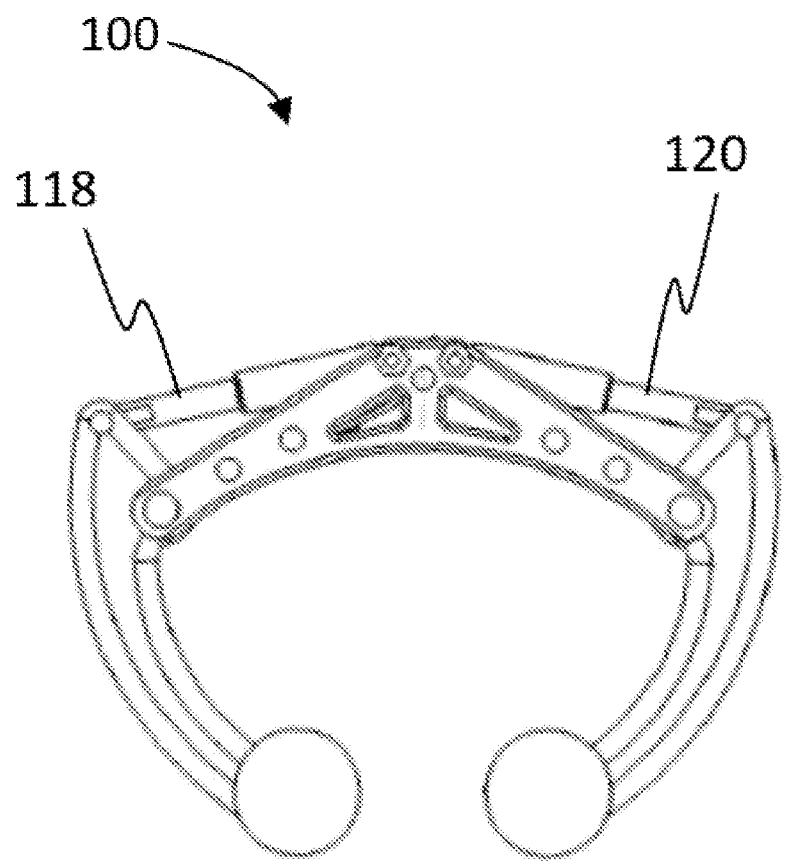

Further, skilled artisans will appreciate that elements in the drawings are illustrated for simplicity and may not have been necessarily been drawn to scale. Furthermore, in terms of the construction of the device, one or more components of the device may have been represented in the drawings by conventional symbols, and the drawings may show only those specific details that are pertinent to understanding the embodiments of the present invention so as not to obscure the drawings with details that will be readily apparent to those of ordinary skill in the art having benefit of the description herein.

DETAILED DESCRIPTION

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

In this specification, the words "print", "printed" and "printing" are used to refer to the making of an original document regardless of the techniques used, and the words "copy" and "copying" to refer to making copies from an original.

It will be understood by those skilled in the art that the foregoing general description and the following detailed description are exemplary and explanatory of the invention and are not intended to be restrictive thereof.

Reference throughout this specification to "an aspect", "another aspect" or similar language means that a particular feature, structure, or characteristic described in connection with the embodiment is included in at least one embodiment of the present invention. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Unless otherwise defined, all technical and scientific terms used herein have the same meaning as commonly understood by one of ordinary skill in the art to which this invention belongs. The system, methods, and examples provided herein are illustrative only and not intended to be limiting.

Embodiments of the present invention will be described below in detail with reference to the accompanying drawings.

FIGS. 1(a)-1(d) show schematics of an electro-mechanical resuscitating apparatus for controlling expansion and compression of a self-inflating bag in accordance with an embodiment of the invention. FIGS. 1(a) and (b) illustrate perspective view of the apparatus 100 and FIGS. 1(c) and (d) illustrate front view of the apparatus 100. The apparatus 100 includes a first supporting arm 102 and a second supporting arm 104, wherein each of the first supporting arm 102 and second supporting arm 104 includes a coupling end 106 and a placement end 108 respectively, wherein a length of the each supporting arm between the coupling end 106 and the placement end 108 conforms to at least a portion of an outer surface area of the self-inflating bag. The apparatus further includes a first coupling arm 110 and a second coupling arm 112 connected to each other through a plurality of connecting elements while maintaining a predetermined distance across respective lengths, wherein the first supporting arm 102 is rotatably fixed at a first end 114 between the first coupling arm 110 and the second coupling arm 112 and the second supporting arm 104 is rotatably fixed at a second end 116 between the first and second coupling arm 112. A first driving mechanism (not shown), and a second driving mechanism (not shown), is coupled to a first shaft 118 and a second shaft 120 respectively, wherein a front end of the first shaft 118 is coupled to the coupling end 106 of the first supporting arm 102 and a front end of the second shaft 120 is coupled to the coupling end 106 of the second supporting arm 104. A controller is communicatively coupled to the first driving mechanism and the second driving mechanism, wherein the controller (not shown) is configured to control the speed and direction of movement of the first shaft 118 and the second shaft 120 via the first driving mechanism and the second driving mechanism respectively, wherein an actuation of the first shaft 118 and second shaft 120 in a first direction enables movement of the placement end 108 of the respective first supporting arm 102 and the second supporting arm 104 toward the self-inflating bag causing compression of the self-inflating bag, wherein an actuation of the first shaft 118 and second shaft 120 in a second direction enables movement of the placement end 108 of the first supporting arm 102 and the second supporting arm 104 away from the self-inflating bag causing expansion of the self-inflating bag. Referring to FIG. 1(*a*), it can be noticed that the first shaft 118 and second shaft 120 of the apparatus 100 are in an open (wide) position such that the suitably held self-inflating bag will be in non-compressed or partially compressed in comparison to the self-inflating bag held between the position of the first shaft 118 and second shaft 120 of the apparatus 100 indicated in FIG. 1(*b*).

In an embodiment, the placement end 108 of each of the first supporting arm 102 and second supporting arm 104 is adapted to support a plurality of rollers 122 to reduce frictional forces between the outer surface of the self-inflating bag and the plurality of rollers 122.

In an embodiment, the plurality of rollers 122 has a silicone coating on respective outer surfaces. To prevent wear of the self-inflating bag surface and to maintain good surface contact, the rollers 122 will be coated with a layer of soft material like silicone. The rollers 122 may have any shape with a smooth contour to minimize localized pressure points while compressing the self-inflating bag. The rollers 122 are provided to minimize contact friction on the self-inflating bag surface, and reduce the force requirement from the motor.

In another embodiment, the apparatus 100 further includes a first holding arm rotatably affixed near to the first end 114 between the between the first coupling arm 110 and second coupling arm 112 and a second holding arm rotatably affixed near to the second end 116 between the between the first coupling arm 110 and second coupling arm 112, wherein the self-inflating bag is supported on the first and second holding arms.

In another embodiment, the apparatus 100 further includes a spring loaded safety mechanism causing the first holding arm and the second holding arm to remain in a locked state while supporting the self-inflating bag.

In another embodiment, the at least one of the first and second driving mechanism comprises at least one of a hydraulic drive mechanism and a motor-based drive mechanism. In an implementation, the apparatus 100 may include a single drive mechanism.

In another embodiment, the length and distance between axes of each of the first supporting arm 102 and second supporting arm 104 are proportional to a diameter of the self-inflating bag.

In another embodiment, the controller is further configured to receive input parameters from a user and control the speed and direction of movement of the first shaft 118 and the second shaft 120 in accordance with the input parameters.

In another embodiment, the compression of the self-inflating bag causes delivery of air or oxygen or both to a patient connected to the self-inflating bag and retraction of the self-inflating bag causes intake of fresh air or a predefined amount of oxygen or both into the self-inflating bag, in accordance with predefined Inspiratory-Expiratory Ratio (IE Ratio). In another embodiment, the controller is configured to perform at least one of: control an amount of expansion and retraction of the self-inflating bag to release a predetermined amount of air towards a patient in accordance with requirements of the patient; initiate actuation of the first and second driving mechanisms to assist in breathing of the patient when a current pressure at an outlet of the self-inflating bag is below a threshold pressure value.

In another embodiment, the apparatus 100 further may include or connected to at least a flow sensor to determine the amount of air released toward the patient, wherein the controller is configured to initiate an alarm when the a released quantity of air is below a threshold quantity of air to be released; and a pressure relief/pop-off valve attached to a delivery end of the self-inflating bag, wherein said valve is configured to prevent air being delivered at excess/un-safe pressure to a patient.

In another embodiment, the apparatus 100 further includes a battery case adapted to be coupled to at least one of the first coupling arm 110 and the second coupling arm 112.

In another embodiment, the apparatus 100 further includes a case encapsulating at least the battery case, the controller, at least a portion of the first supporting arm 102 and second supporting arm 104, at least a portion of the first coupling arm 110 and second coupling arm 112 and at least a portion of the first and second holding arms.

In an embodiment, the apparatus 100 may include suitable warning indicators and alarms for low-battery, charging from an un-compatible power source, excess pressure in the airway circuit or excessive resistance for the movement of the first shaft 118 and second shaft 120. Alarm may be triggered for any undesired change in parameters predetermined by the controller and set by the user.

In an embodiment, the movement of first shaft 118 and second shaft 120 is synchronized and driven by a pair of gears and wherein one of these gears is connected to a motor which is controlled by the controller.

Figure 2:
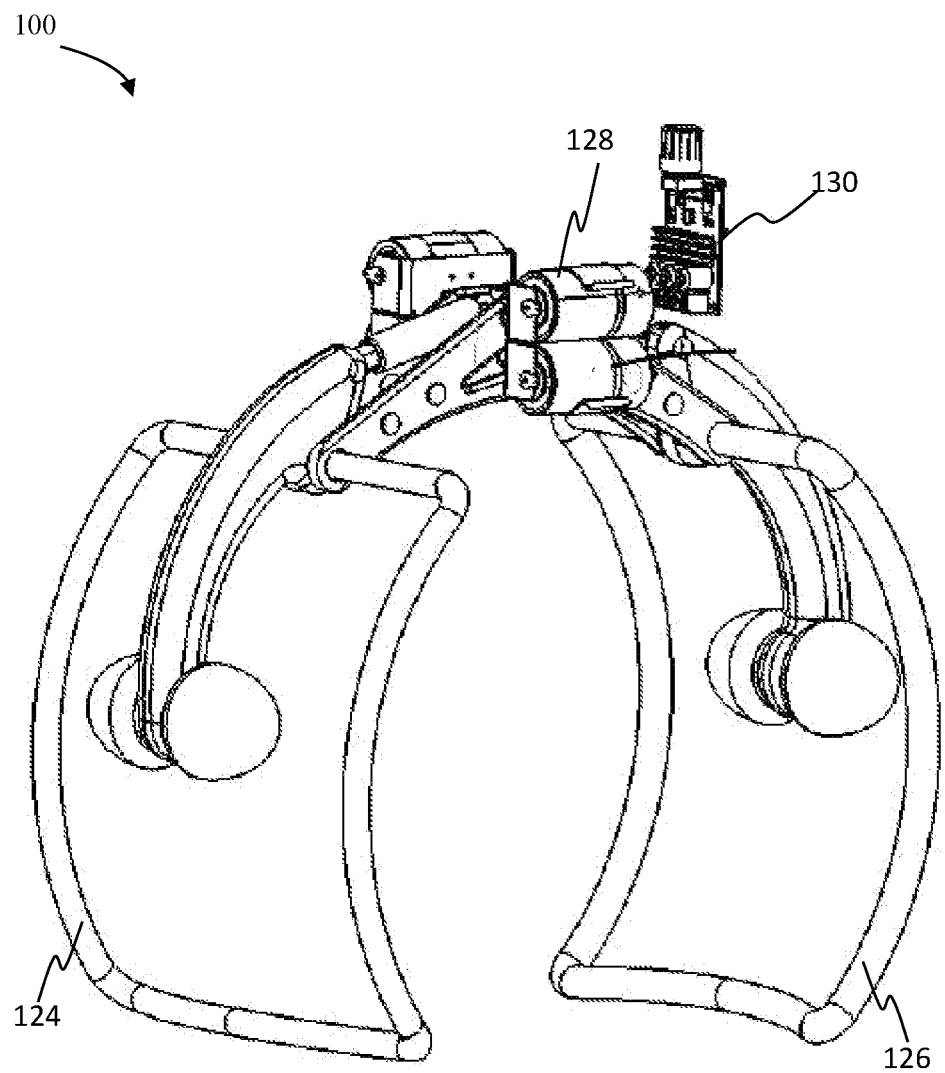
FIG. 2 illustrates another schematic view of the apparatus illustrated in FIGS. 1(a)-1(d) in accordance with an embodiment of the invention.

Referring to FIG. 2, another schematic view of the apparatus illustrated in FIG. 1 is provided. FIG. 2 illustrates the support for holding the self-inflating bag. As can be noticed that a first holding arm 124 is rotatably affixed near to the first end 114 between the between the first coupling arm 110 and second coupling arm 112 and a second holding arm 126 is rotatably affixed near to the second end 116 between the between the first coupling arm 110 and second coupling arm 112, wherein the self-inflating bag is supported on the first and second holding arms. The first holding arm 124 and second holding arm 126 are together referred to as the Bag Holder. The power for controlling the operation of the apparatus 100 may be drawn either from a Direct Current from an adapter connected to an AC wall supply or an inbuilt rechargeable battery-pack/case. As can be noticed, a battery pack case 128 may be provided and adapted to be coupled to at least one of the first coupling arm 110 and the second coupling arm 112 for supplying power for operating the apparatus 100. The battery case may include one or more power batteries for providing power to the driving mechanisms. The batteries may include rechargeable batteries. The batteries enable wireless operation during transit and power-outages. In an embodiment, the Power for operation of the apparatus 100 can be drawn from a standard power supply. FIG. 2 also illustrates the controller 130, essentially a micro-controller, adapted to be coupled to the first driving mechanism and the second driving mechanism. The controller 130 includes one or more processing circuitry that are embedded with suitable instructions for controlling the movements of the first shaft 118 and second shaft 120.

Figure 3:
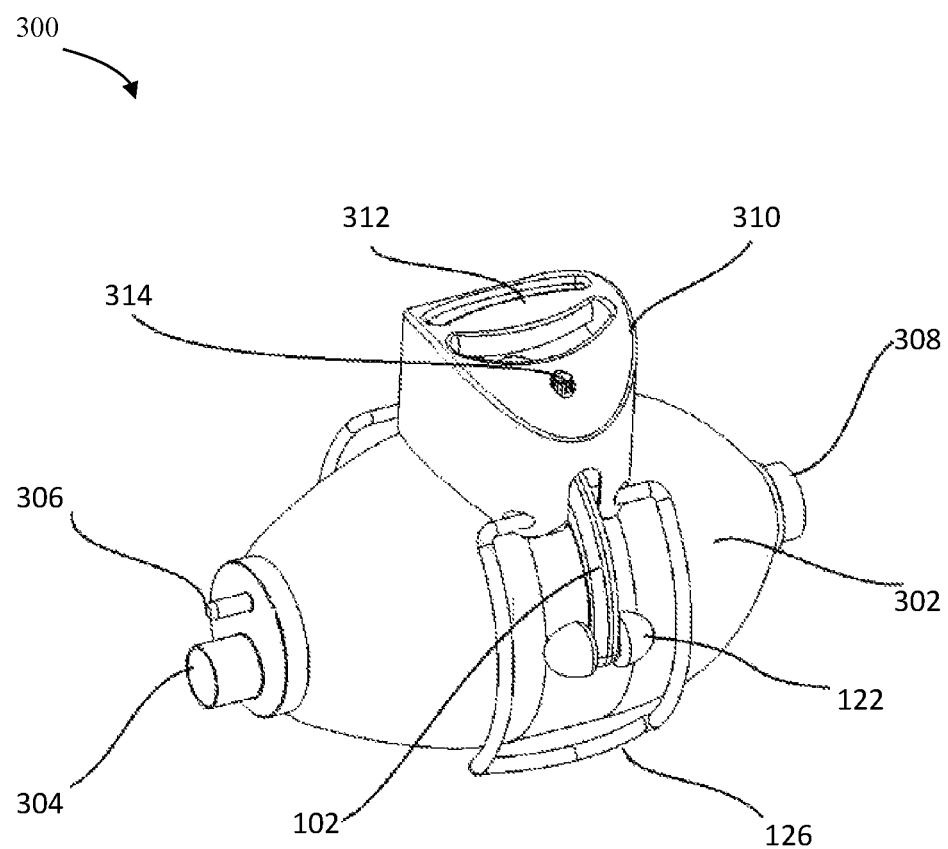
FIG. 3 illustrates a schematic of the apparatus 100 illustrated in FIG. 1(a), 1(b), 1(c), 1(d), and 2, holding a self-inflating bag, in accordance with an embodiment of the present invention.

FIG. 3 illustrates a schematic of the apparatus 100 illustrated in FIGS. 1 and 2, holding a self-inflating bag, in accordance with an embodiment of the present invention. As can be seen in FIG. 3, the system 300 shows a 302 is suitably held by the apparatus 100 using the bag-holder. The self-inflating bag 302 includes an air inlet 304 and oxygen inlet 306 that is configured to draw fresh air or oxygen from the atmosphere or from an external supply. An air outlet 308 is provided to supply air or oxygen or air oxygen mixture stored in the self-inflating bag to the patient in need. The apparatus 100 further includes a case/casing 310 encapsulating at least the battery case 128, the controller 130, at least a portion of the first supporting arm 102 and second supporting arm 104, at least a portion of the first coupling arm 110 and second coupling arm 112 and at least a portion of the first and second holding arms. The casing 310 acts as a housing for covering the one or more components of the apparatus 100. The casing 310 is provided with a suitable handle 312 for holding the system 300 or apparatus 100 along with or without the self-inflating bag 302. A control knob 314 on the casing is further provided for controlling the speed, rate of movement of the first shaft 118 and second shaft 120 (not shown) of apparatus 100, thereby controlling compression and decompression of the self-inflating bag, and in particularly controlling the supply of the air or oxygen to the patient. The rollers 122 forming part of the apparatus 100 are suitably placed to maintain good surface contact with the self-inflating bag 302 and are provided with a silicone coating on respective outer surfaces to prevent wear of the self-inflating bag surface.

Figure 4:
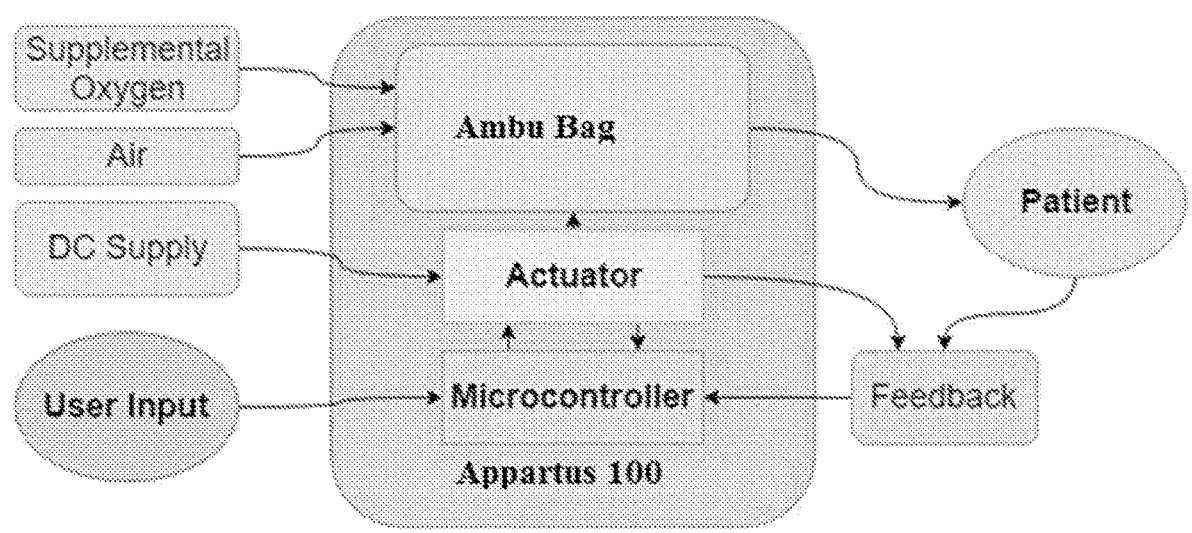
FIG. 4 illustrates a block diagram of a system level architecture in accordance with an embodiment of the present invention.

Referring to FIG. 4, a block diagram of a system level architecture in accordance with an embodiment of the present invention is provided. The system level architecture shall be read in line with the description provided in FIGS. 1-3 for explaining the operation of the present invention. The driving mechanisms (actuators), preferably, DC gear motors, are the prime driver for system, whose actuation is controlled by a Controller 130 (microcontroller 130), based on the input from the user, entered through an interface. The DC motors function to actuate the first and second shift with their suitable fitted rollers 122, against the surface of the self-inflating bag, to cause a compression of the bag and driving air into the patient's lung through a connected endotracheal tube, working against the airway resistance. The first shaft 118 and second shaft 120 retract after the required compression, allowing the self-inflating bag to inflate and intake a fresh charge of air or supplemental oxygen or air-oxygen mixture. The DC motors reverse direction during this phase. This compressing and retraction (expansion) action will be performed at various strokes and rates based on the patient requirements. Once the desired delivery of air or air-oxygen is done, the self-inflating bag inflates in the same manner as if it was manually squeezed and released thereby taking a fresh charge of air. The timing of the compression and retraction of the first shaft 118 and second shaft 120, the stroke-rate, is defined by the microcontroller 130 taking in the parameters such as the user-set frequency and the Inspiratory-Expiratory (IE) ratio. The IE Ratio of ventilation can be controlled by controlling the motors' forward and reverse speeds with the microcontroller 130. The user can have control over setting the IE Ratio according to the patient's requirement. The amount of collapse decides the air volume delivered to the patient while the flow rate will be controlled by the stroke rate. These strokes repeat in a cyclic manner, delivering the positive pressure for ventilation.

In a mandatory ventilation mode (default mode), the actuation of the air delivery will be time triggered (on a particular frequency set by the user). Similarly, the actuation of the self-inflating bag ends when the set time is over, and the cycle is repeated. The present invention system may incorporate an assist control mode which initiates a new inspiratory cycle and helps in patient's breathing when the patient takes a spontaneous breath. This operation will be triggered by sensing the negative pressure at the exit of the AMBU-bag (during breath initiation). Similar to mandatory ventilation mode, it is time cycled and is adjusted for new frequency based on patient's spontaneous breath. The present invention may also include a provision for delivering the required fractional inspired oxygen concentration.

The system may include suitable safety features in place to ensure smooth operation and to avoid complications. The Micro-controller 130 uses information from the feedback sensors system as a feedback to control motor, alarm, and display. Motor controls the airflow by taking the input from sensor and user through the microcontroller 130. Alarm gets triggered if any undesired change in parameters occurs. The flow sensor senses the amount of air delivered and raises an alarm in case of deviation from the preset conditions. In addition, proximity sensors will be used to measure the stroke thereby having a check on the breaths delivered for a given period of time. The system may also include a pressure cut-off valve which breaks the air delivery cycle when the system exceeds a certain pressure limit.

All the sensing and actuating is controlled and governed by the micro-controller 130. The system may also include a display to show the real time parameters. The threshold values of all the parameters are set by the user on the microcontroller 130 using buttons in a control interface. In an implementation, a web-based interface and dashboard may also be provided.

The mechanical motion of the Ambu compression and retraction mechanism as described above is synthesized to deliver end values of pressure and frequency in-par with that delivered when given by a trained and experienced medical professional. In effect, the device simulates the effects of hand compression from a trained professional during ventilation. Since the present invention uses the self-inflating bag, the system is significantly cheaper than existing ventilators that provide IPPV mode ventilation. Self-inflating bags are widely used and there are well established systems in place for procurement, sterilization and disposal of these even at low resource settings. This ensures that patients requiring a ventilator support get access to a safer alternative for prolonged manual ventilation at the peripheries, with the help of the present invention. The treatment-cost burden on the patient and society is also significantly reduced.

The present invention may be used in: Hospital based respiratory support system (includes resuscitation, Ventilation among others); ICU based respiratory support system (includes resuscitation, Ventilation among others); and Home based respiratory support system (includes resuscitation, Ventilation among others). The present system has low maintenance, is easy to use and intuitive for users and is affordable. The present system supplies air to the patient by automatically compressing the self-inflating bag at conditions set by the user. By having a compressing mechanism with DC motor as a prime driver, a purely automated ventilation system is achieved using the present invention. The present device has low maintenance, as it does not use air pumps or air-filters which are the components most susceptible to failure in conventional ventilators. Also, the device hosts safety features for limiting pressure and alerting the medical staff and caretakers of any abnormality in the devices' function.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature of the invention.

We claim:

1. An electro-mechanical resuscitating apparatus for controlling expansion and compression of a self-inflating bag, the apparatus comprising:
    a first supporting arm and a second supporting arm, wherein each of the first supporting arm and the second supporting arm includes a coupling end and a placement end respectively, wherein a length of the each of the first supporting arm and the second supporting arm between the coupling end and the placement end conforms to at least a portion of an outer surface area of the self-inflating bag;
    a first coupling arm and a second coupling arm connected to each other while maintaining a predetermined distance across respective lengths, wherein the first supporting arm is rotatably fixed at a first end of the first and second coupling arms and the second supporting arm is rotatably fixed at a second end of the first and second coupling arms;
    a first driving mechanism and a second driving mechanism coupled to a first shaft and a second shaft respectively, wherein a front end of the first shaft is coupled to the coupling end of the first supporting arm and a front end of the second shaft is coupled to the coupling end of the second supporting arm; and
    a controller communicatively coupled to the first driving mechanism and the second driving mechanism, wherein the controller is configured to control the speed and direction of movement of the first shaft and the second shaft via the first driving mechanism and the second driving mechanism respectively, wherein:
    an actuation of the first shaft and the second shaft in a first direction enables movement of the placement ends of the respective first supporting arm and the second supporting arm against surface of the self-inflating bag causing compression of the self-inflating bag;
    an actuation of the first shaft and the second shaft in a second direction enables movement of the placement ends of the first supporting arm and the second supporting arm to retract causing retraction of the self-inflating bag; and
    the placement end of each of the first and second supporting arms is adapted to support a plurality of rollers to reduce frictional forces between the outer surface of the self-inflating bag and the plurality of rollers.

2. The apparatus as claimed in claim 1, wherein the plurality of rollers have a silicone coating on respective outer surfaces.

3. The apparatus as claimed in claim 1, further comprising at least one of:
    a first holding arm rotatably affixed near the first end between the first and second coupling arms;
    a second holding arm rotatably affixed near the second end between the between the first and second coupling arms, wherein the self-inflating bag is supported on the first and second holding arms; and
    a spring loaded safety mechanism causing the first holding arm and the second holding arm to remain in a locked state while supporting the self-inflating bag.

4. The apparatus as claimed in claim 1, wherein at least one of the first and second driving mechanism comprises at least one of a hydraulic drive mechanism and a motor-based drive mechanism.

5. The apparatus as claimed in claim 1, wherein length and distance between axes of each of the first and second supporting arms are proportional to a diameter of the self-inflating bag.

6. The apparatus as claimed in claim 1, wherein the controller is further configured to receive input parameters from a user and control the speed and direction of movement of the first shaft and the second shaft in accordance with the input parameters.

7. The apparatus as claimed in claim 1, wherein compression of the self-inflating bag causes delivery of air or oxygen or both to a patient connected to the self-inflating bag and retraction of the self-inflating bag causes intake of fresh air or a predefined amount of oxygen or both into the self-inflating bag, in accordance with pre-defined Inspiratory-Expiratory Ratio (IE Ratio).

8. The apparatus as claimed in claim 1, wherein the controller is configured to perform at least one of:
    control an amount of expansion and retraction of the self-inflating bag to release a predetermined amount of air towards a patient in accordance with requirements of the patient; and
    initiate actuation of the first and second driving mechanisms to assist in breathing of the patient when a current pressure at an outlet of the self-inflating bag is below a threshold pressure value.

9. The apparatus as claimed in claim 1, further comprising at least one of:
    a flow sensor to determine the amount of air released toward the patient, wherein the controller is configured to initiate an alarm when a released quantity of air is below a threshold quantity of air to be released; and
    a pressure relief/pop-off valve attached to a delivery end of the self-inflating bag, wherein the pressure relief/pop-off valve is configured to prevent air being delivered at an excess and an unsafe pressure to a patient.

10. A method comprising providing the electro-mechanical resuscitating apparatus of claim 1.

11. An electro-mechanical resuscitating apparatus for controlling expansion and compression of a self-inflating bag, the apparatus comprising:

a first supporting arm and a second supporting arm, wherein each of the first supporting arm and the second supporting arm includes a coupling end and a placement end respectively, wherein a length of the each of the first supporting arm and the second supporting arm between the coupling end and the placement end conforms to at least a portion of an outer surface area of the self-inflating bag;

a first coupling arm and a second coupling arm connected to each other while maintaining a predetermined distance across respective lengths, wherein the first supporting arm is rotatably fixed at a first end of the first and second coupling arms and the second supporting arm is rotatably fixed at a second end of the first and second coupling arms;

a first driving mechanism and a second driving mechanism coupled to a first shaft and a second shaft respectively, wherein a front end of the first shaft is coupled to the coupling end of the first supporting arm and a front end of the second shaft is coupled to the coupling end of the second supporting arm; and a controller communicatively coupled to the first driving mechanism and the second driving mechanism, wherein the controller is configured to control the speed and direction of movement of the first shaft and the second shaft via the first driving mechanism and the second driving mechanism respectively, wherein:

an actuation of the first shaft and the second shaft in a first direction enables movement of the placement ends of the respective first supporting arm and the second supporting arm against surface of the self-inflating bag causing compression of the self-inflating bag;

an actuation of the first shaft and the second shaft in a second direction enables movement of the placement ends of the first supporting arm and the second supporting arm to retract causing retraction of the self-inflating bag; and the apparatus further comprises at least one of:
 a first holding arm rotatably affixed near the first end of the first and second coupling arms;
 a second holding arm rotatably affixed near the second end of the first and second coupling arms, wherein the self-inflating bag is supported on the first and second holding arms; and
 a spring loaded safety mechanism causing the first holding arm and the second holding arm to remain in a locked state while supporting the self-inflating bag.

12. The apparatus according to claim 11, wherein the placement end of each of the first and second supporting arms is adapted to support a plurality of rollers to reduce frictional forces between the outer surface of the self-inflating bag and the plurality of rollers.

13. The apparatus according to claim 12, wherein the plurality of rollers have a silicone coating on respective outer surfaces.

14. The apparatus according to claim 11, wherein at least one of the first and second driving mechanism comprises at least one of a hydraulic drive mechanism and a motor-based drive mechanism.

15. The apparatus according to claim 11, wherein length and distance between axes of each of the first and second supporting arms are proportional to a diameter of the self-inflating bag.

16. The apparatus according to claim 11, wherein the controller is further configured to receive input parameters from a user and control the speed and direction of movement of the first shaft and the second shaft in accordance with the input parameters.

17. The apparatus according to claim 11, wherein compression of the self-inflating bag causes delivery of air or oxygen or both to a patient connected to the self-inflating bag and retraction of the self-inflating bag causes intake of fresh air or a predefined amount of oxygen or both into the self-inflating bag, in accordance with pre-defined Inspiratory-Expiratory Ratio (IE Ratio).

18. The apparatus according to claim 11, wherein the controller is configured to perform at least one of:
 control an amount of expansion and retraction of the self-inflating bag to release a predetermined amount of air towards a patient in accordance with requirements of the patient; and
 initiate actuation of the first and second driving mechanisms to assist in breathing of the patient when a current pressure at an outlet of the self-inflating bag is below a threshold pressure value.

19. The apparatus according to claim 11, further comprising at least one of:
 a flow sensor to determine the amount of air released toward the patient, wherein the controller is configured to initiate an alarm when a released quantity of air is below a threshold quantity of air to be released; and
 a pressure relief/pop-off valve attached to a delivery end of the self-inflating bag, wherein the pressure relief/pop-off valve is configured to prevent air being delivered at an excess and an unsafe pressure to a patient.

20. An electro-mechanical resuscitating apparatus for controlling expansion and compression of a self-inflating bag, the apparatus comprising:

a first supporting arm and a second supporting arm, wherein each of the first supporting arm and the second supporting arm includes a coupling end and a placement end respectively, wherein a length of the each of the first supporting arm and the second supporting arm between the coupling end and the placement end conforms to at least a portion of an outer surface area of the self-inflating bag;

a first coupling arm and a second coupling arm connected to each other while maintaining a predetermined distance across respective lengths, wherein the first supporting arm is rotatably fixed at a first end of the first and second coupling arms and the second supporting arm is rotatably fixed at a second end of the first and second coupling arms;

a first driving mechanism and a second driving mechanism coupled to a first shaft and a second shaft respectively, wherein a front end of the first shaft is coupled to the coupling end of the first supporting arm and a front end of the second shaft is coupled to the coupling end of the second supporting arm; and a controller communicatively coupled to the first driving mechanism and the second driving mechanism, wherein the controller is configured to control the speed and direction of movement of the first shaft and the second shaft via the first driving mechanism and the second driving mechanism respectively, wherein:

an actuation of the first shaft and the second shaft in a first direction enables movement of the placement ends of the respective first supporting arm and the second supporting arm against surface of the self-inflating bag causing compression of the self-inflating bag;

an actuation of the first shaft and the second shaft in a second direction enables movement of the placement ends of the first supporting arm and the second supporting arm to retract causing retraction of the self-inflating bag;

the placement end of each of the first and second supporting arms is adapted to support a plurality of rollers to reduce frictional forces between the outer surface of the self-inflating bag and the plurality of rollers; and the plurality of rollers have a silicone coating on respective outer surfaces.

* * * * *